United States Patent
Heald et al.

(10) Patent No.: US 8,145,501 B1
(45) Date of Patent: Mar. 27, 2012

(54) SYSTEM AND METHOD FOR PERFORMING PHARMACY PRODUCT FILLING USING NON-REGISTERED PHARMACISTS

(75) Inventors: Susan Heald, Buffalo Grove, IL (US); Amylu Miller, Wauconda, IL (US); Charles Goodall, Hawthorn Woods, IL (US)

(73) Assignee: Walgreen Co., Deerfield, IL (US)

( * ) Notice: Subject to any disclaimer, the term of this patent is extended or adjusted under 35 U.S.C. 154(b) by 621 days.

(21) Appl. No.: 12/248,769

(22) Filed: Oct. 9, 2008

(51) Int. Cl.
*G06Q 50/00* (2012.01)

(52) U.S. Cl. .................................. 705/2; 705/3

(58) Field of Classification Search ........... 705/2
See application file for complete search history.

(56) References Cited

U.S. PATENT DOCUMENTS

| | | |
|---|---|---|
| 4,457,772 A | 7/1984 | Haynes et al. |
| 4,852,001 A | 7/1989 | Tsushima et al. |
| 5,053,970 A | 10/1991 | Kurihara et al. |
| 5,072,383 A | 12/1991 | Brimm et al. |
| 5,260,868 A | 11/1993 | Gupta et al. |
| 5,289,370 A | 2/1994 | Lirov |
| 5,337,919 A | 8/1994 | Spaulding et al. |
| 5,548,518 A | 8/1996 | Dietrich et al. |
| 5,559,710 A | 9/1996 | Shahraray et al. |
| 5,597,995 A | 1/1997 | Williams et al. |
| 5,615,121 A | 3/1997 | Babayev et al. |
| 5,619,991 A | 4/1997 | Sloane |
| 5,630,070 A | 5/1997 | Dietrich et al. |
| 5,737,539 A | 4/1998 | Edelson et al. |
| 5,737,728 A | 4/1998 | Sisley et al. |
| 5,748,907 A | 5/1998 | Crane |
| 5,758,095 A | 5/1998 | Albaum et al. |
| 5,765,139 A | 6/1998 | Bondy |
| 5,790,785 A | 8/1998 | Klug et al. |
| 5,797,515 A | 8/1998 | Liff et al. |
| 5,801,755 A | 9/1998 | Echerer |
| 5,826,236 A | 10/1998 | Narimatsu et al. |
| 5,826,252 A | 10/1998 | Wolters, Jr. et al. |
| 5,845,255 A | 12/1998 | Mayaud |
| 5,852,259 A | 12/1998 | Yanase et al. |
| 5,907,493 A | 5/1999 | Boyer et al. |
| 5,911,687 A | 6/1999 | Sato et al. |
| 5,915,240 A | 6/1999 | Karpf |
| 5,924,074 A | 7/1999 | Evans |
| 5,946,883 A | 9/1999 | Yuyama et al. |
| 5,954,640 A | 9/1999 | Szabo |
| 5,963,911 A | 10/1999 | Walker et al. |
| 5,970,462 A | 10/1999 | Reichert |

(Continued)

FOREIGN PATENT DOCUMENTS

EP     0 921 488 A1     6/1999

(Continued)

OTHER PUBLICATIONS

Office action for U.S. Appl. No. 11/252,947 dated Mar. 17, 2010.

(Continued)

*Primary Examiner* — Gerald J. O'Connor
*Assistant Examiner* — Hiep V Nguyen
(74) *Attorney, Agent, or Firm* — Francis C. Kowalik; Marshall, Gerstein & Borun LLP; Randall G. Rueth

(57) ABSTRACT

The method and system provides a single-role pharmacy product filling workflow that coordinates filling and inspection to increase the accuracy and consistency of released pharmacy products.

21 Claims, 12 Drawing Sheets

U.S. PATENT DOCUMENTS

| | | | |
|---|---|---|---|
| 5,987,519 | A | 11/1999 | Peifer et al. |
| 6,067,524 | A | 5/2000 | Byerly et al. |
| 6,078,912 | A | 6/2000 | Buerger et al. |
| 6,112,182 | A | 8/2000 | Akers et al. |
| 6,202,080 | B1 | 3/2001 | Lu et al. |
| 6,202,923 | B1 | 3/2001 | Boyer et al. |
| 6,208,973 | B1 | 3/2001 | Boyer et al. |
| 6,256,550 | B1 | 7/2001 | Wu et al. |
| 6,266,655 | B1 | 7/2001 | Kalyan |
| 6,294,999 | B1 | 9/2001 | Yarin et al. |
| 6,311,163 | B1 | 10/2001 | Sheehan et al. |
| 6,330,491 | B1 | 12/2001 | Lion |
| 6,347,329 | B1 | 2/2002 | Evans |
| 6,364,517 | B1 | 4/2002 | Yuyama et al. |
| 6,370,841 | B1 | 4/2002 | Chudy et al. |
| 6,381,577 | B1 | 4/2002 | Brown |
| 6,397,190 | B1 | 5/2002 | Goetz |
| 6,421,650 | B1 | 7/2002 | Goetz et al. |
| 6,438,451 | B1 | 8/2002 | Lion |
| 6,463,417 | B1 | 10/2002 | Schoenberg |
| 6,464,142 | B1 | 10/2002 | Denenberg et al. |
| 6,477,442 | B1 | 11/2002 | Valerino, Sr. |
| 6,493,427 | B1 | 12/2002 | Kobylevsky et al. |
| 6,496,427 | B2 | 12/2002 | Kojima et al. |
| 6,523,009 | B1 | 2/2003 | Wilkins |
| 6,539,281 | B2 | 3/2003 | Wan et al. |
| 6,564,121 | B1 | 5/2003 | Wallace et al. |
| 6,625,952 | B1 | 9/2003 | Chudy et al. |
| 6,665,740 | B1 | 12/2003 | Mason, Jr. et al. |
| 6,711,460 | B1 | 3/2004 | Reese |
| 6,735,497 | B2 | 5/2004 | Wallace et al. |
| 6,741,724 | B1 | 5/2004 | Bruce et al. |
| 6,874,684 | B1 | 4/2005 | Denenberg et al. |
| 6,947,900 | B2 | 9/2005 | Giordano, III et al. |
| 7,058,584 | B2 | 6/2006 | Kosinski et al. |
| 7,111,780 | B2 | 9/2006 | Broussard et al. |
| 7,139,639 | B2 | 11/2006 | Broussard et al. |
| 7,801,642 | B2 * | 9/2010 | Ansari et al. .................. 700/240 |
| 2001/0009005 | A1 | 7/2001 | Godin et al. |
| 2002/0019786 | A1 | 2/2002 | Gonzalez et al. |
| 2002/0052770 | A1 | 5/2002 | Podrazhansky |
| 2002/0062175 | A1 | 5/2002 | Lion |
| 2002/0062230 | A1 | 5/2002 | Morag et al. |
| 2002/0120573 | A1 | 8/2002 | McCormick |
| 2002/0153411 | A1 | 10/2002 | Wan et al. |
| 2002/0188467 | A1 | 12/2002 | Eke |
| 2002/0198454 | A1 | 12/2002 | Seward et al. |
| 2003/0074234 | A1 | 4/2003 | Stasny |
| 2003/0109950 | A1 | 6/2003 | Andrade et al. |
| 2003/0149599 | A1 | 8/2003 | Goodall et al. |
| 2003/0179287 | A1 | 9/2003 | Kozic et al. |
| 2003/0225595 | A1 | 12/2003 | Helmus et al. |
| 2004/0019794 | A1 | 1/2004 | Moradi et al. |
| 2004/0117046 | A1 | 6/2004 | Colle et al. |
| 2004/0133705 | A1 | 7/2004 | Broussard et al. |
| 2004/0172289 | A1 | 9/2004 | Kozic et al. |
| 2004/0220829 | A1 | 11/2004 | Baharav et al. |
| 2004/0221034 | A1 | 11/2004 | Kausik et al. |
| 2004/0260577 | A1 | 12/2004 | Dahlin et al. |
| 2005/0075902 | A1 | 4/2005 | Wager et al. |
| 2005/0125798 | A1 | 6/2005 | Peterson |
| 2006/0041330 | A1 | 2/2006 | Ansari et al. |
| 2006/0149587 | A1 | 7/2006 | Hill et al. |
| 2006/0253346 | A1 * | 11/2006 | Gomez .......................... 705/28 |
| 2006/0276933 | A1 | 12/2006 | Chavez et al. |
| 2006/0287906 | A1 | 12/2006 | McGillin |

FOREIGN PATENT DOCUMENTS

| | | |
|---|---|---|
| JP | 361217880 A | 9/1986 |
| WO | WO-96/13790 A1 | 5/1996 |
| WO | WO-01/08393 A1 | 2/2001 |

OTHER PUBLICATIONS

Final Office action for U.S. Appl. No. 11/253,252 dated Mar. 5, 2010.
Final Office action for U.S. Appl. No. 11/252,776 dated Apr. 22, 2010.
Final Office action for U.S. Appl. No. 11/253,253 dated Mar. 9, 2010.
"The Virtual Pharmacist," *Rural Electric*, vol. 60, No. 6, Mar. 2002, p. 20.
"CVS, Merck-Medco in E-commerce Alliance," Chain Drug Review, 21(18):2 (1999).
Colchamiro, "Independents Look To Go Online," American Druggist, Sep. 1999, pp. 1-3.
McNaughton, "Can Net Drugstores Outpace The Chains?" CNET News.com, Feb. 24, 1999, 1 page.
Walgreens On-line Prefills (Website Printout Packet-printed Jul. 5, 2006) archived as Jun. 17, 1998, p. 1-13.
Wolverton, "Online Pharmacies Partner for Power," CNET News. com, Oct. 8, 1999, pp. 1-2.
"Name Change Reflects CVS' Commitment to E-commerce," *Chain Drug Review*, 21(15):2 (1999).
"Optimize your Enterprise for Maximum Profitability," NDCHEALTH, May 5, 2005, 4 pages.
"File Locking," www.wikipedia.org/wili/file_locking obtained via web.archive.com.
Office Action issued in U.S. Appl. No. 11/252,776 dated Sep. 28, 2009.
Office Action issued in U.S. Appl. No. 11/252,947 dated Sep. 2, 2009.
Office Action issued in U.S. Appl. No. 11/253,096 dated Jun. 10, 2009.
Office Action issued in U.S. Appl. No. 11/253,253 dated Jul. 20, 2009.
Final Office Action issued in U.S. Appl. No. 11/252,775 dated Sep. 29, 2009.
Final Office Action issued in U.S. Appl. No. 11/252,759 dated Jan. 15, 2010.
Final Office Action issued in U.S. Appl. No. 11/253,185 dated Jan. 8, 2010.
Office Action issued in U.S. Appl. No. 11/253,252 dated Sep. 3, 2009.
Final Office action for U.S. Appl. No. 11/252,947 dated Oct. 4, 2010.
Office action for U.S. Appl. No. 12/248,774 dated Oct. 28, 2010.
Office action for U.S. Appl. No. 11/252,759 dated Aug. 6, 2010.

* cited by examiner

SYSTEM AND METHOD FOR PERFORMING PHARMACY PRODUCT FILLING USING NON-REGISTERED PHARMACISTS

FIELD OF INVENTION

The present invention generally relates to a process and system for managing pharmacy product prescription filling in a pharmacy network.

BACKGROUND

Pharmacy prescription products may generally be processed by registered pharmacists hired to take responsibility for the accuracy and consistency of the pharmacy filling process. However, pharmacist time may be more efficiently spent in an advisory role to a customer, which may educate patients/customers about their prescriptions and improve customer service. In this situation, product filling may be more economically billed to non-registered pharmacists or technicians. One of the most important roles in the filling process is product verification, in which both the type of pharmacy product and the quantity or amount of the product must be inspected. Existing systems may not be adequate in supporting pharmacy product prescription filling by non-registered pharmacists or technicians.

SUMMARY OF THE INVENTION

The method and system of the claims enables a single non-registered pharmacist (also known as a technician) or multiple non-registered pharmacists to fill a prescription with less reliance on a registered pharmacist to be involved in the filling and verification process. In particular, the method and system uses a pharmacy computing system to regulate the timing of the filling process and to provide an interactive inspection process (between technician and computer) to increase accuracy and consistency of a single role filling process. In one embodiment, a registered pharmacist may still be used in a supervisory aspect without requiring the registered pharmacist to be involved in every filling process.

DRAWINGS

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Figure 1:
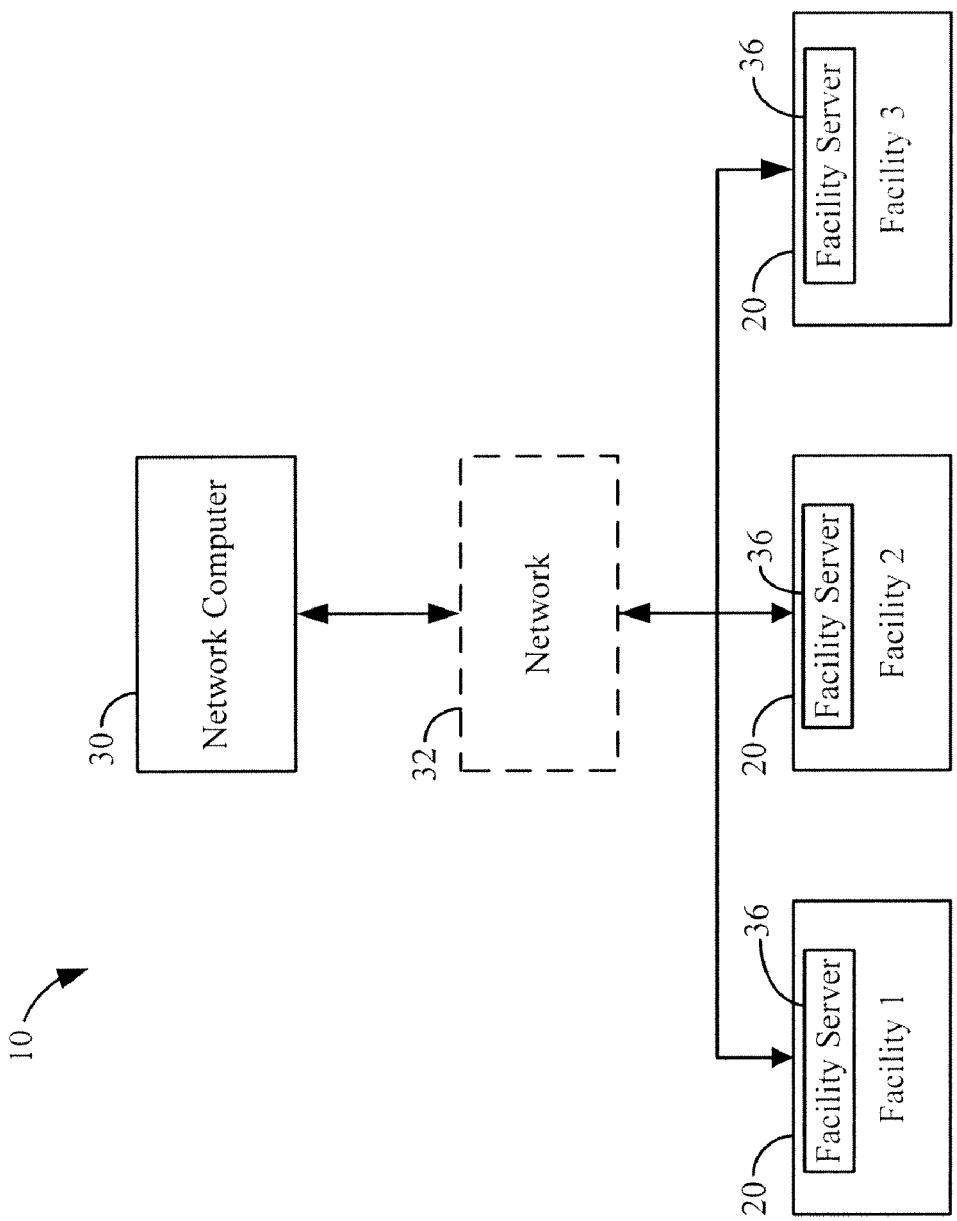
FIGS. 1-3 illustrate block diagrams of a computing system that may operate in accordance with the described embodiments.

FIG. 1 illustrates an embodiment a data network 10 including a first group of pharmacies 20 operatively coupled to a network computer 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, combinations of these, etc. Additionally, the network 32 may include a plurality of network computers or server computers (not shown), each of which may be operatively interconnected in a known manner. Where the network 32 comprises the Internet, data communication may take place over the network 32 via an Internet communication protocol.

The network computer 30 may be a server computer of the type commonly employed in networking solutions. The network computer 30 may be used to accumulate, analyze, and download pharmacy data. For example, the network computer 30 may periodically receive data from each of the pharmacies 20 indicative of information pertaining to a prescription order, billing information, employee data, etc. The pharmacies 20 may include one or more facility servers 36 that may be utilized to store information for a plurality of customers/employees/accounts/etc. associated with each facility.

Although the data network 10 is shown to include one network computer 30 and three pharmacies 20, it should be understood that different numbers of computers and pharmacies may be utilized. For example, the network 32 may include a plurality of network computers 30 and dozens of pharmacies 20, all of which may be interconnected via the network 32. According to the disclosed example, this configuration may provide several advantages, such as, for example, enabling near real time uploads and downloads of information as well as periodic uploads and downloads of information. This provides for a primary backup of all the information generated in the process of updating and accumulating pharmacy data.

Figure 2:
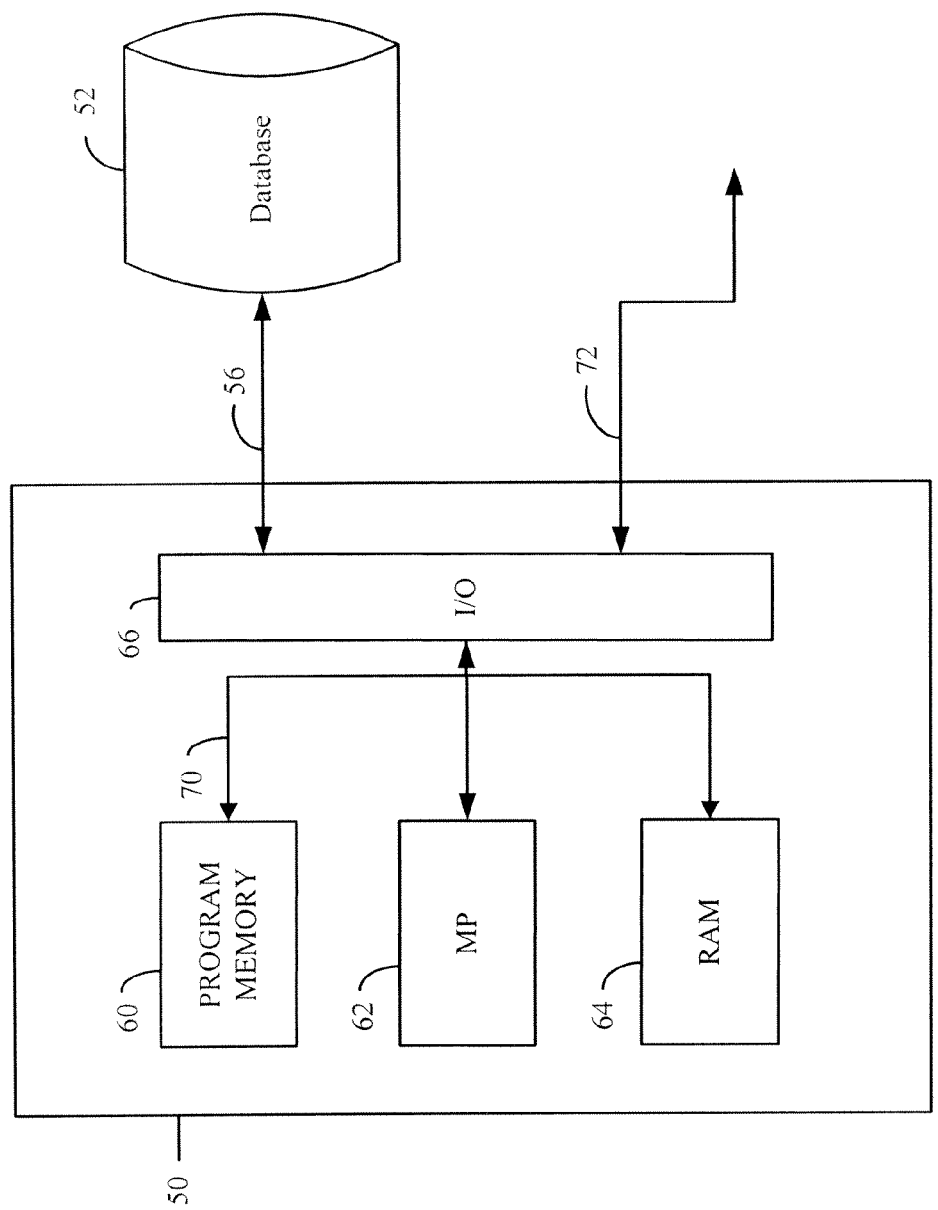

FIG. 2 is a schematic diagram of one possible embodiment of the network computer 30 shown in FIG. 1. The network computer 30 may have a controller 50 that is operatively connected to a database 52 via a link 56. It should be noted that, while not shown, additional databases may be linked to the controller 50 in a known manner.

The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAMs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
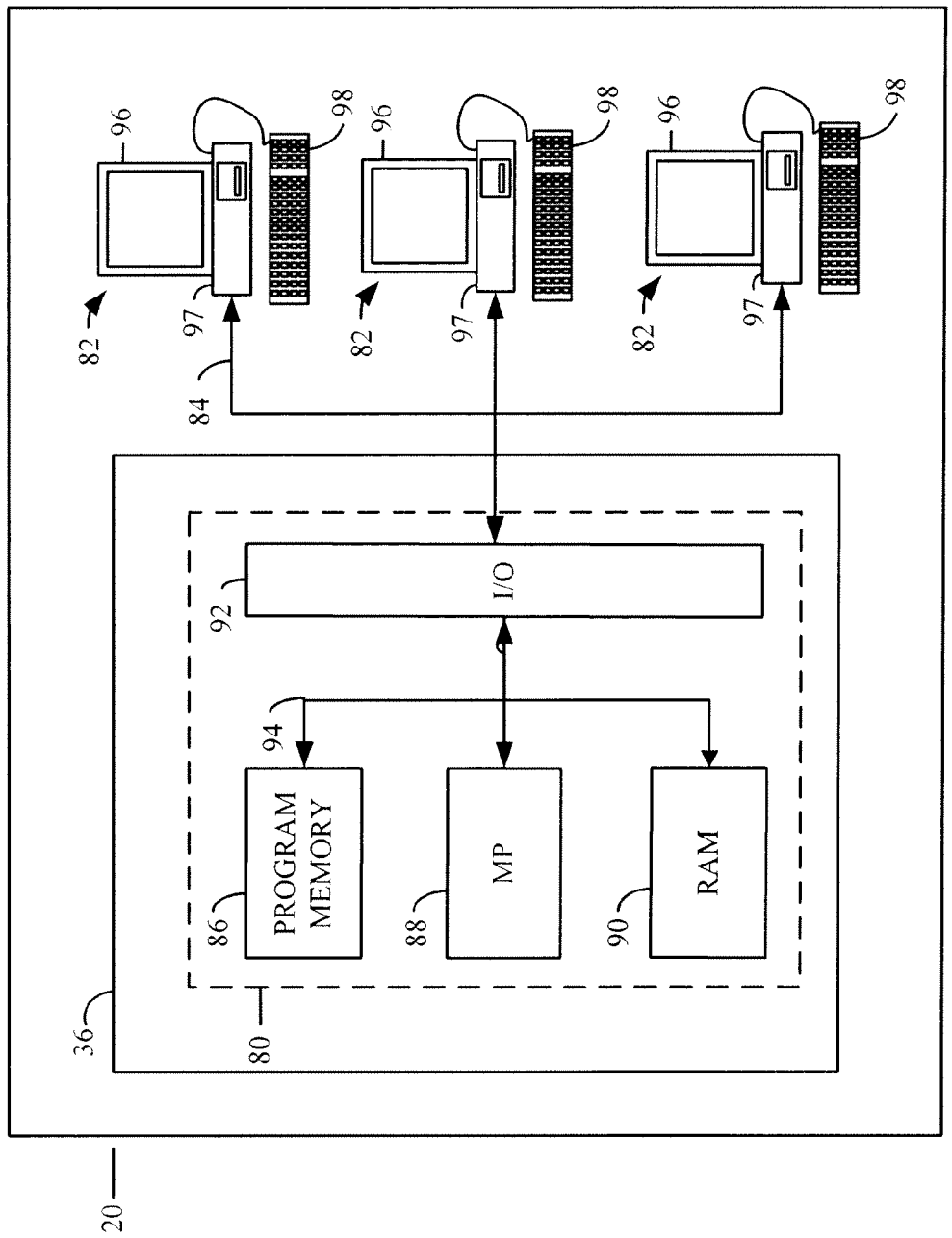

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the data connections present in a typical pharmacy. For exemplary purposes, one design of a pharmacy is described below, but it should be understood that numerous other designs may be utilized.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAMs 90 and multiple programs memories 86. Although the I/O circuit 92 is shown as a single block, the I/O circuit 92 may include a number of different types of I/O circuits. The RAM(s) 90 and programs memories 86 may also be implemented as semiconductor memories, magnetically readable memories, and/or optically readable memories, for example.

The client device terminals 82 may include a display 96, a controller 97, a keyboard 98 as well as a variety of other input/output devices (not shown) such as a scanner, printer, mouse, touch screen, track pad, track ball, isopoint, voice recognition system, scale, digital camera, etc. Each client device terminal 82 may be signed onto and occupied by a pharmacy employee to assist them in performing their duties. Pharmacy employees may sign onto a client device terminal 82 using any generically available technique, such as entering a user name and password. If a pharmacy employee is required to sign onto a client device terminal 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high end computer with a large storage capacity, one or more fast microprocessors, and one or more high speed network connections. Conversely, relative to a typical facility server 36, each client device terminal 82 may typically include less storage capacity, a single microprocessor, and a single network connection.

Figure 4:
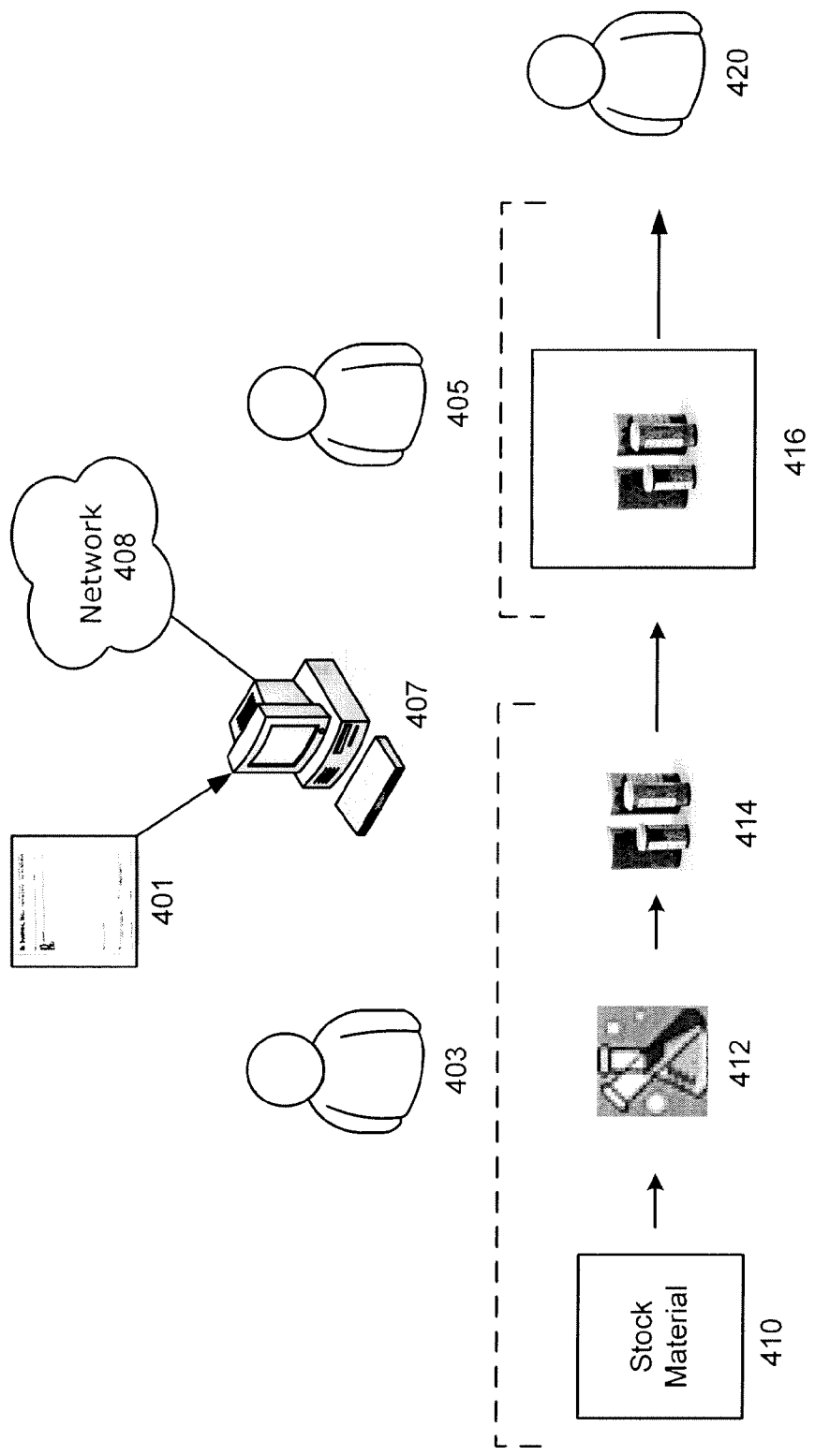
FIG. 4 illustrates a traditional pharmacy workflow.

FIG. 4 illustrates an existing pharmacy system. Generally, a first pharmacy retail store 400 may receive a pharmacy product prescription 401 for filling. A pharmacy person, such as a technician (a non-registered pharmacist) 403 or a registered pharmacist 405 may receive or access the prescription and begin processing a prescription order using a first computer 407. While a single registered pharmacist 405 may perform in all steps of the prescription filling process, it may be more common for a pharmacist 405 to be involved primarily with a pharmacy product verification process while a technician 403, or non-registered pharmacist, performs other steps required to physically fill a delivery container with a type and quantity of a pharmacy product. In particular, a technician 403 may be involved in procuring stock material 410, performing any mixing or chemical preparation 412 related to the pharmacy product prescription, and filling a delivery container with a type and quantity of a pharmacy product 414. The filled delivery container may then be placed in a verification queue 416 awaiting unregistered pharmacist 405 to inspect the type and quantity contained in the delivery container before release of the delivery container to a customer 420.

It may be likely that customers favor a pharmacy retail store that provides better customer service. This improved customer service may be provided in the form of available face time with a registered pharmacist who is better able to guide a customer through their prescription process and to answer clinical/technical questions about their prescription and/or treatment, something a non-registered pharmacist may not be able to do. While filling prescription orders continues to take a portion of registered pharmacist time, face-to-face time with customers may be limited. To help alleviate the involvement of registered pharmacists in the filling process and to redistribute the work required for inspection and verification to a non-registered pharmacist or technician, the system may provide an authentication process to ensure accountability and a plurality of mechanisms to improve the accuracy of a technicians physical inspection process.

Figure 5:
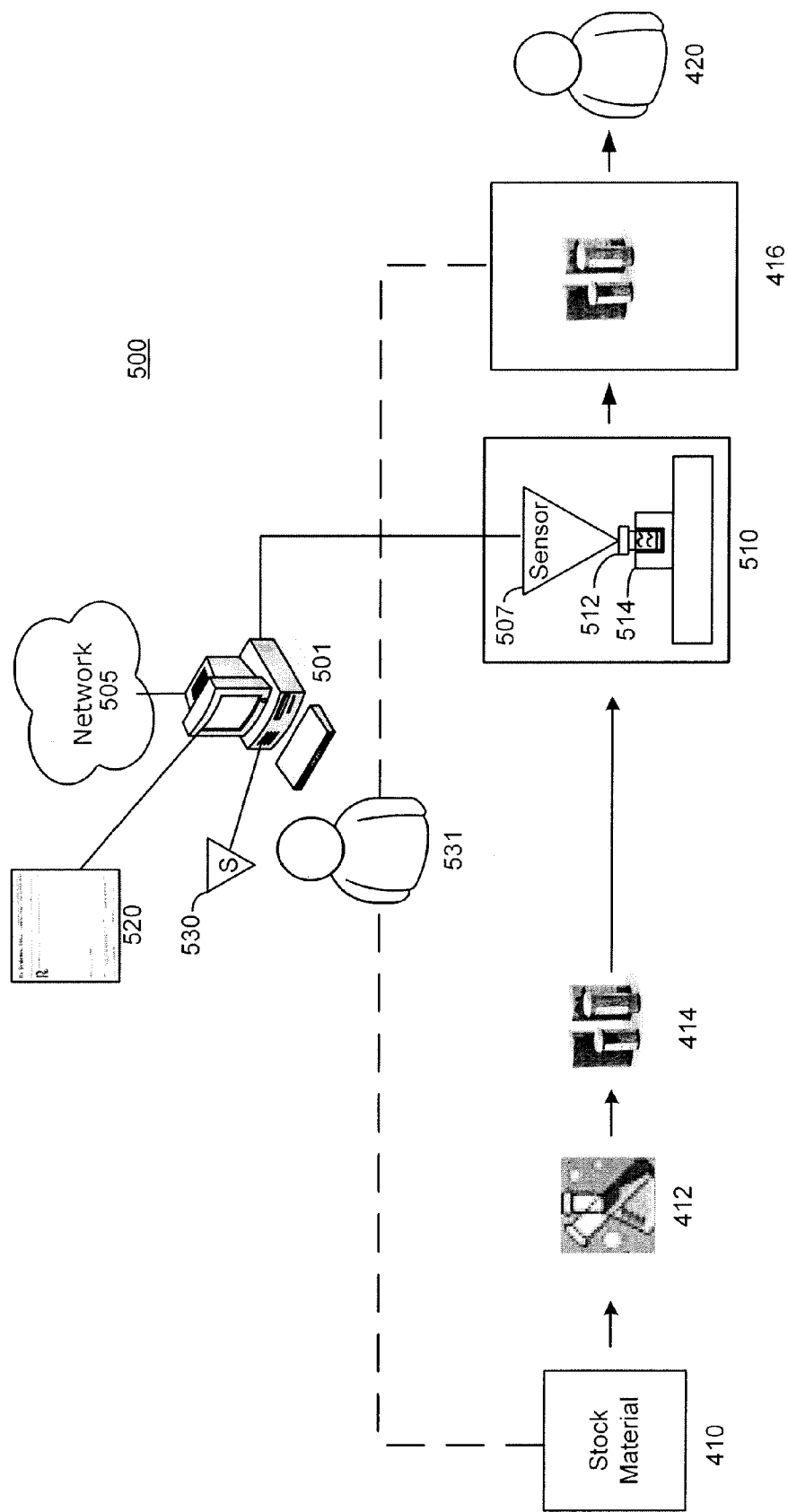
FIG. 5 illustrates a system embodiment of a pharmacy product prescription filling process involving a non-registered pharmacist or technician.

FIG. 5 illustrates an embodiment of a pharmacy computing system 500 for allowing a non-registered pharmacist or technician to perform a pharmacy product filling process that includes product verification. A pharmacy computing system may include a first computer 501 disposed in a first pharmacy resource, such as a pharmacy retail store. The first computer 501 may be communicatively coupled to a network 505. The network 505 may communicatively connect the first computer 501 to a plurality of other computers located in other pharmacy retail stores, where the plurality of computers are a part of the pharmacy computing system 500. The first pharmacy resource may include a plurality of computers, including a second computer (not shown in FIG. 5), communicatively coupled to the network 505 in addition to the first computer 501. Accordingly, the first computer 501 may communicate with any of the plurality of other computers in the first pharmacy resource via, for example, the network 505 or a different communication connection.

FIG. 5 illustrates that a sensor device 507 may be connected to the pharmacy computing system 500. While FIG. 5 illustrates that the sensor device 507 is connected to the first computer 501, the sensor device 507 may be connected to the pharmacy computing system using a second computer of the pharmacy resource or directly connected to the network (e.g., the sensor may contain its own processing unit and network interface device). Sensor device 507 may include any sensor for detecting or measuring a physical parameter of a pharmacy product. The sensor device 507 may be disposed within a larger automated inspection device 510 for accepting or receiving a pharmacy product, where the sensor device 507 may be used on a received pharmacy product contained in a delivery container 512. In one embodiment, the automated inspection device 510 may include a receptacle 514 for accepting the delivery container 512. The delivery container may contain a type and quantity of a pharmacy product that is suppose to correspond with a pharmacy product prescription 520 received at the first computer 501. The automated inspection device 510 may be configured to include a housing and other necessary support structure to provide necessary isolation from the external environment in which the automated inspection device 510 is disposed. This isolation may be necessary to provide accurate sensor readings.

Among various types of sensors, the sensor device 507 may be a weight sensor, a spectrographic sensor, olfaction sensor, pH sensor, toughness sensor, tensile strength sensor, composition sensor, temperature sensor, humidity sensor, image sensor, etc. The automated inspection device 510 may include a plurality of sensor devices 507 including the ones listed above. For example, in one embodiment, a first sensor may be an infrared sensor used to detect a quantity of product in the delivery container and a second sensor may be a spectrographic sensor used to identify the type of product contained in the delivery container. The sensor device 507 may provide data to the pharmacy computing system on a measured physical parameter for the sensor. This data may be received at the first computer 501 and displayed on the first computer for a user such as a technician to review. The sensor data may be used in calculations made by the first computer as further discussed below.

FIG. 5 further illustrates that a second sensor device 530 may be communicatively coupled to the pharmacy computing system 500. The second sensor device 530 may be used to authenticate or identify a technician 531 at the first computer 501. For example, the second sensor 530 may be a biometric sensor that detects one or more of a plurality of identifying characteristics of the technician 531 at the first computer 501. Biometric sensors may include retina scanners, fingerprint scanners, etc.

Figure 6:
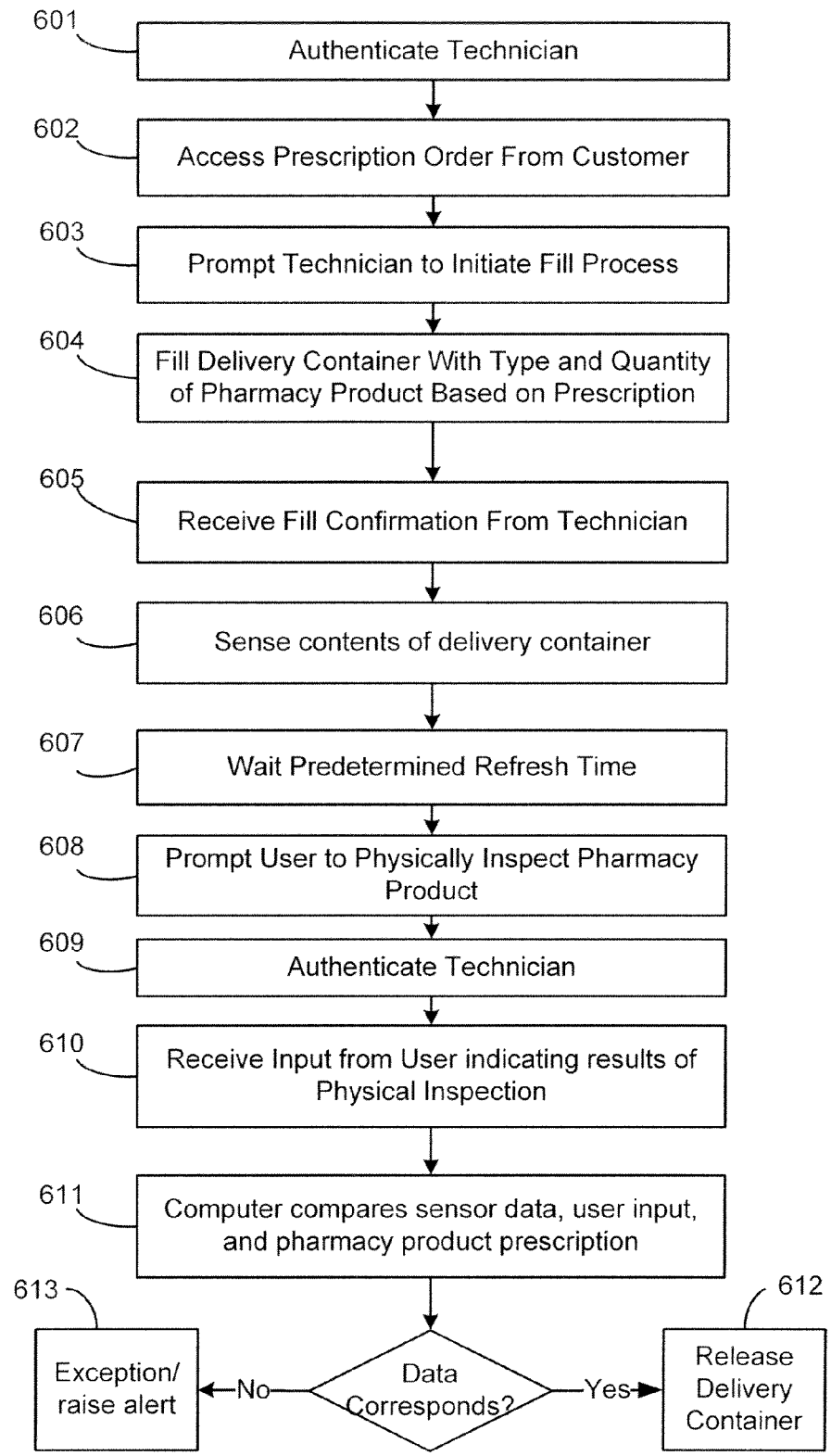
FIG. 6 illustrates a process embodiment of the technician filling and verification process.

FIG. 6 illustrates a process for filling a pharmacy product prescription using a pharmacy computing system such as the one illustrated in FIG. 5. In particular, FIG. 6 illustrates a process that involves a single non-registered pharmacist, or technician. A computing system, such as the computing system illustrated in FIG. 5 may be programmed to implement the process of FIG. 6.

An authentication process 601 may be used to determine whether a technician is authorized to execute the filling process. The authentication process 601 may be implemented at different and multiple times during the described fill process. For example, authentication of the technician may be initiated at the beginning of the described filling process, as illustrated in FIG. 6, before a technician is even prompted to physically fill the delivery container 603 or at other times. As discussed above, one of the important aspects for reassigning portions of the filling process from a registered pharmacist to a technician is accountability. To place responsibility for each filled prescription order on a particular technician, authentication may be necessary. Thus, in one embodiment, the computer may be programmed to require that an authentication session be established with a user and to associate a particular technician to a currently processed pharmacy product prescription order.

Generally, authentication is the process of verifying that a user is who that user claims to be. Authentication may be implemented using a number of different processes. One technique uses credentials, such as a user name and password pair. In this case, authentication involves a process by which technician credentials are verified. Sessions in which a technician logs into the computer are authenticated sessions. In one embodiment, a technician remains authenticated as long as the user name and password remains active.

Determining the status, e.g., active or inactive, of a credential pair provides an additional degree of authentication. In one embodiment, a session may be active for a predetermined period of time, after which, the session is no longer active and a user must again provide credentials for continued processing. One variation of this embodiment is that the session may be active until a user logs out of the computing system. In another embodiment, each computer access may require providing credentials. In this case, the active session period may be viewed as having zero duration. There is a compromise between duration of the session validity (i.e., how long the session is active) and user convenience. For example, while a zero validity period (in which each access to the computer requires credentials to be entered) provides increased security, a time zero validity period decreases the convenience and ease in which a user is able to use the pharmacy computing system. In one embodiment, the validity time of the authentication system may be adjusted based on the nature of the pharmacy product prescription and statistics on authentication failures.

To continue the filling process, a pharmacy product prescription order may be accessed 602. The first pharmacy product prescription may be received at the computer from a second computer of the pharmacy network, or the first pharmacy product prescription may be originated by the first computer (e.g., by pharmacy resource personnel). A technician may then be prompted to initiate filling (physical) of the prescription order 603. Displaying the first pharmacy product prescription (e.g., on a monitor of the first computer) may serve to prompt the technician to begin filling a type and a quantity of pharmacy product based on the first pharmacy product prescription 604. Alternatively or in addition, the first computer may be programmed to print out a label indicating the pharmacy product prescription order which serves to prompt the technician to begin filling the pharmacy product. Also, prompting the technician to fill a pharmacy product prescription may merely involve the computing system waiting for an input 605 to initiate the next block 606 of the process. Similarly, at a block 606 the computing system may sense the contents of the delivery container (further discussed below) and this sensing process may require placing a filled delivery container near a sensor (e.g., placing the delivery container in a sensing receptacle).

To fill the pharmacy product prescription, the technician may obtain an empty delivery container and attach a label corresponding to the pharmacy product prescription order. The technician may then fill the delivery container with a type and an amount of pharmacy product corresponding to the prescription order 604.

After the technician finishes physically filling the delivery container, the computer may be programmed to receive a confirmation from the technician the delivery container is filled 605. The technician may provide an indication to the pharmacy computing system that the technician is finished filling the delivery container 605 by, for example, inputting a finished value into the first computer. The computer may be programmed to pause execution of further steps in the process until the fill confirmation is received from the technician.

After providing the finish indication to the computer, the technician may then use sensors to scan the delivery container 606. This may be performed, for example, by placing the delivery container into an automated inspection device containing a set of sensors. In one embodiment, the computer may be programmed to prompt the user to scan the delivery container. As discussed above with reference to FIG. 5, the automated inspection device may include a set of sensors used to detect and measure a physical parameter of the pharmacy product in the delivery container. For example, the automated inspection device may detect or measure the type and/or quantity of a pharmacy product contained in the delivery container. In one embodiment, the first computer may be programmed to acknowledge receipt of the technician finish indication and prompt the user to place the delivery container into the automated inspection device, after which the contents of the delivery container may be scanned (or sensed) by a sensor device. In an alternative embodiment, the first computer may be programmed to control the sensor device or automated inspection device such that the sensor device may not operate until the technician's finish indication is received.

After the contents of the delivery container are inspected using the automated inspection device 606, the first computer may prompt the technician or non-registered pharmacist to physically inspect the contents of the delivery container including inspecting the type and/or quantity of the pharmacy product contained in the delivery container 608. After or during the physical inspection by the technician, the computer may be programmed to receive an input from the technician with the results of the inspection 610. The results may indicate, for example, the type and quantity of pharmacy product in the delivery container under inspection.

In one embodiment, the first computer may be programmed to require a certain wait time or time delay between the time that the technician fills the pharmacy product and the time in which the technician performs the physical inspection 607. The delay may be introduced to prevent technician bias from affecting the inspection process. For example, a technician that just finished physically filling the delivery container may be biased by the technician's memory of the previous filling step. For example, the technician may be biased by his previous count on quantity of product from the previous filling step and may be influenced by his memory to enter the same count during the physical inspection process. Thus, in some embodiments, the first computer may be programmed with a wait delay that may be randomly set or set and/or adjusted by an appropriate party (e.g., by a software developer, a physician, a pharmacist, non-registered pharmacist, etc.).

The wait delay may generally be set based on a prescreening test for a particular technician. For example, routine tests based on memory and bias may be performed on a technician, the results of which may determine a duration in which memory bias may be sufficiently reduced for a particular user. This technician specific duration may then be associated with a technician's authentication profile. Thus, for example, in one embodiment, when a particular technician authenticates to the pharmacy computing system, the delay used in the process may be set based on the identity of the technician (e.g., based on the technician provided credentials).

The wait delay may start from the moment the technician enters information indicating that the physical fill is finished. The wait delay may be set to include the time necessary for the automated sensing step to be performed. Moreover, the wait delay may be determined based on whether the filling process requires a technician to fill a first prescription before filling a second prescription or whether the technician is allowed to physically fill a plurality of pharmacy product prescriptions. In one embodiment, the delay may be adjusted based on when the automated inspection process is initiated or how long the automated inspection process takes to finish. In one embodiment the wait delay may be the period beginning when the first computer prompts the user to begin a physical inspection. In one embodiment, the wait delay may start when the first computer allows a technician to input the results of the technician's physical inspection of the contents of the delivery container.

In addition to memory bias from the prior filling process, a technician may be biased or influenced by other events such as a display of the actual prescription. Thus, in one embodiment, further mechanisms may be used to provide an interaction between the technician and computer to elicit more accurate inspections. These mechanisms are referred to herein as interaction mechanisms. In one embodiment, the computer may prompt technician inspection without displaying or otherwise providing data on the pharmacy product prescription corresponding to the product in the delivery container. In this manner, the technician may not be influenced or biased to provide data corresponding to the actual prescription, but instead, perform an accurate and independent inspection of the delivery container.

Figure 7:
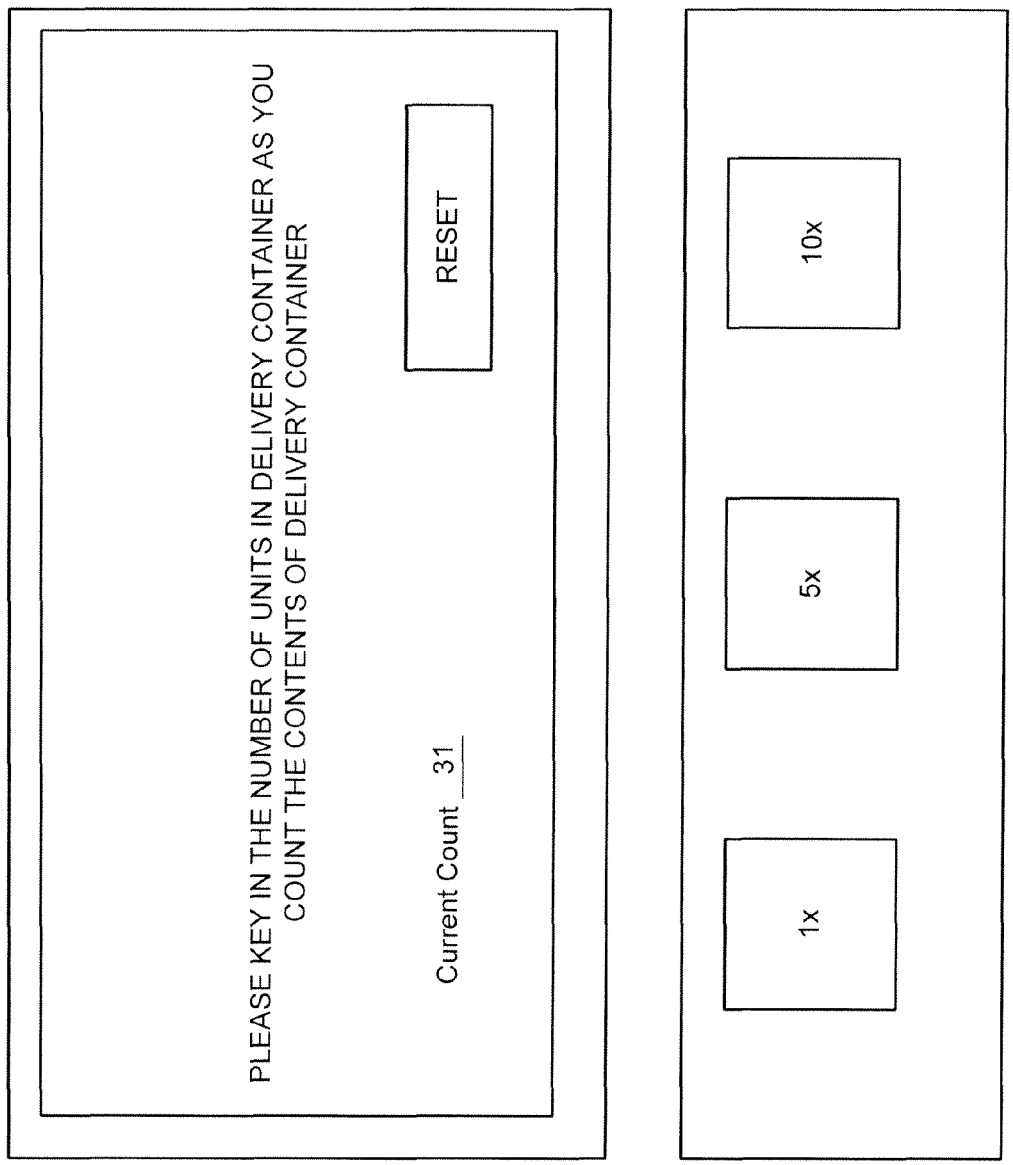
FIG. 7 illustrates an embodiment of an inspection keyboard.

In an embodiment illustrated in FIG. 7, the computer may be programmed to provide keys 701-703 that correspond to particular multiples of units of pharmacy product. For example, a first key may correspond to a single unit count 701, while a second key may correspond to 5 units 702, a third key may correspond to 10 units 703, etc. A corresponding display on the first computer may be illustrated as 705 to prompt the user to use the buttons to count the quantity of product in the delivery container. Thus, while the technician is performing a physical count of the product in the delivery container, the technician must repeatedly press a key to enter his count. While an embodiment of the system may allow a technician to simply input a total count or number corresponding to the technicians count of the pharmacy product, another embodiment may prevent the technician from entering a single total and instead require the technician to press a count key to indicate the quantity of pharmacy product. A reset option 707 may be provided to the technician to reset the count. In this manner, the coordinated interaction of the user count may promote a more accurate quantity measurement of the delivery container contents.

Figure 8:
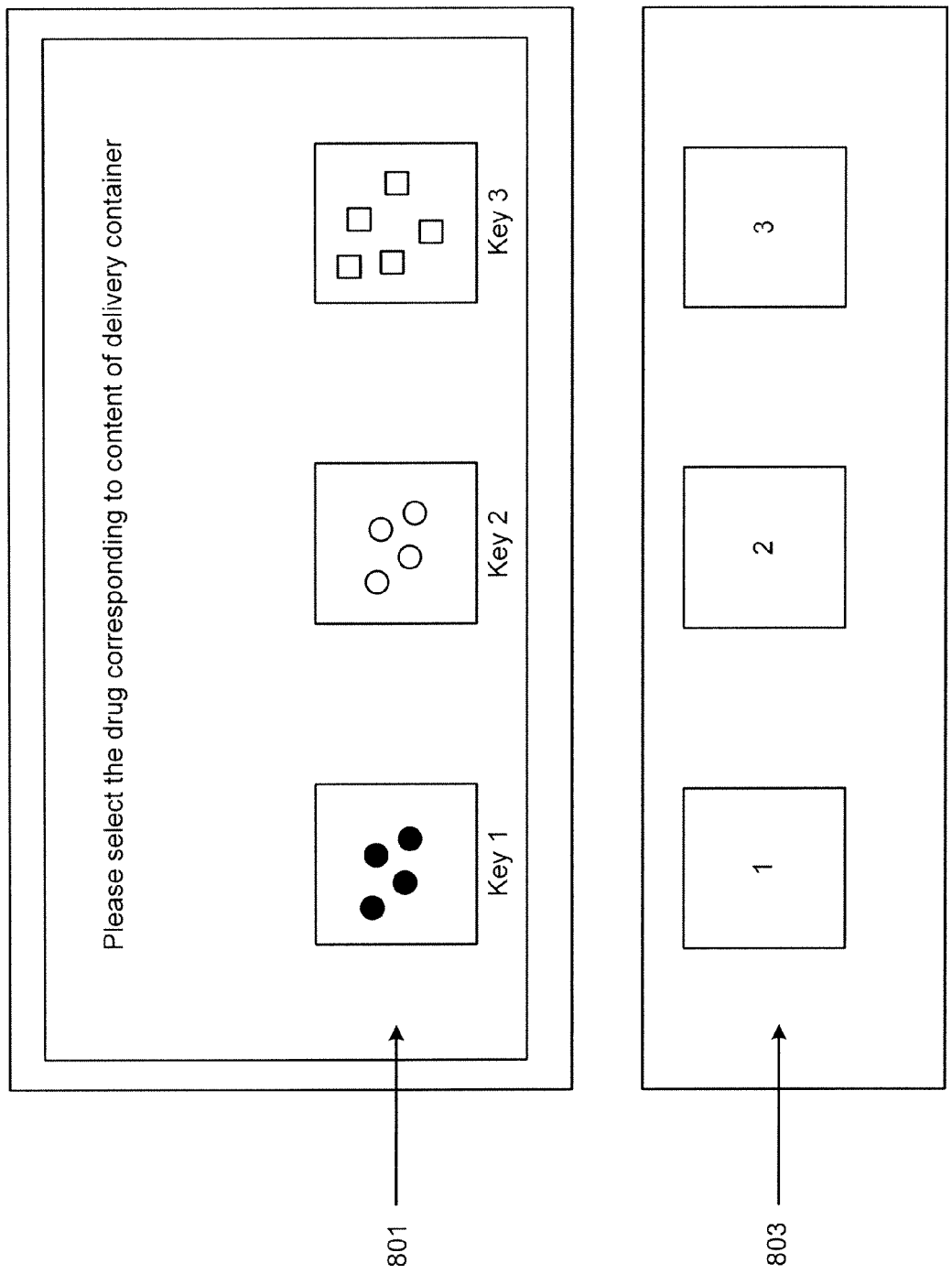
FIG. 8 illustrates an embodiment of a product type selection screen.

FIG. 8 illustrates another embodiment which may be used to remove influence of prior memory bias on the technician performing a product type inspection (i.e., a determination of the type of pharmacy product contained in the delivery container). In FIG. 8, the computer may display a plurality of images of pharmacy products 801, where one image is of the intended pharmacy product in the delivery container (i.e., the image corresponds to the pharmacy product prescription for that delivery container). In this embodiment, the technician may be required to select an image of the intended pharmacy product based on matching the image to the contents of the delivery container a designated input key 802. In another embodiment, no information is provided to the technician by the computer and instead, the computer prompts the technician to provide a description of the pharmacy product (e.g., size, color, markings, etc.) based on the technician's observation. In this manner, a more independent inspection may be elicited from the technician. In one embodiment, where multiple pharmacy products are being filled and processed, the type of confirmation prompted by the first computer may change for each delivery container being inspected. For example, a random input process may be used by the first computer.

In one embodiment, the first computer may require an additional authentication process to verify the identity of the technician 609. For example, credentials may be required after the automated inspection process is performed to verify that the same technician that performed the initial physical filling is the same technician that is performing the physical inspection, thus ensuring the accountability of the technician to the particular pharmacy product prescription. In another embodiment, the additional authentication process may be initiated before a prompt is given to the technician to inspect the product.

By providing the above-described wait delay and interaction mechanisms, the technician's inspection accuracy may be increased while bias from previous steps may be reduced.

After readings from the automated inspection device 606 and measurements from a technician performing a physical inspection of the delivery container contents 608, the first computer may compare the data from the automated inspection device, the technician entered inspection, and the actual pharmacy product prescription to determine whether the type and quantity of pharmacy product in the delivery container corresponds with the type and quantity of pharmacy product in the actual pharmacy product prescription 611. If the data corresponds, then the delivery container may be released to the customer 612. If there is a mismatch in the information between any of the data, then an exception may be thrown 613

The exception may be handled a number of ways. In one embodiment, the exception may prompt an additional physical inspection by the technician and/or an additional inspection using the automated inspection machine. If an error in physical inspection is discovered and the product is actually correct in the delivery container, the delivery container may be released to the customer. If an error occurs with filling (e.g., wrong product type or wrong quantity), then the delivery container contents may be discarded and the process restarted for the prescription. In any of the above embodiments, a registered pharmacist may be alerted (e.g., using a screen lockout, an email, etc.) to a discrepancy and the registered pharmacist may be given the option to interrupt the process and bypass any exception.

Described further below are alternative embodiments that may be used to provide a pharmacy product filling process that includes verification/inspection that reduces the need for involvement of a registered pharmacist.

In one embodiment, the same technician that physically fills the delivery container may be required to finish the prescription filling process. In other words, in this embodiment, the technician that filled the delivery container must be the same technician that performs an actual inspection of the delivery container. In this embodiment, when an authentication period ends and the physical inspection has not yet been initiated or finished, then a second authentication may be required with the pharmacy computing system before the pharmacy computing system continues executing instructions to prompt inspection or to accept or receive inspection results from the technician. This authentication may ensure that the same technician is accountable for a single prescription. This embodiment may correspond to the policy of a particular pharmacy.

Figure 9:
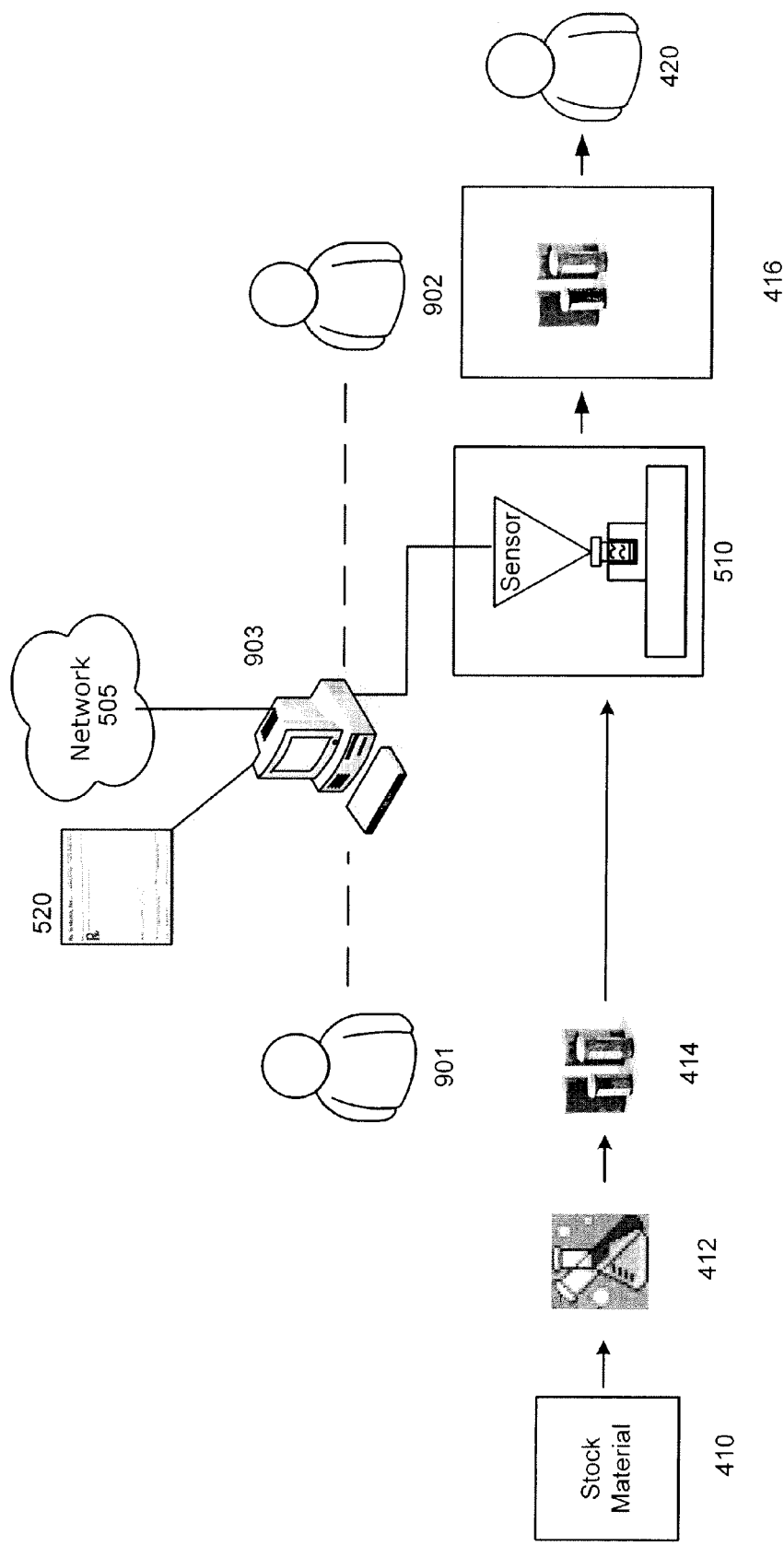
FIG. 9 illustrates an embodiment of the system using a single computer and two technicians.

In one embodiment, two or more technicians may be used for filling a single prescription. FIG. 9 illustrates a system in which two technicians, or non-registered pharmacists, may perform the prescription filling process. In this embodiment, because there is no bias from a previous filling experience (since the technician who filled the container may not be the same technician that inspects the container), the mandatory delay period may not be required. For example, a first technician 901 may perform the physical filling of the delivery container while a second technician 902 may perform physical inspection and verification of the contents of the delivery container before release of the delivery container to a customer. In this embodiment, a first authentication session may be used to authenticate the first technician to the pharmacy computing system, while a second authentication session may be used to authenticate a second technician to the pharmacy computing system. In one embodiment, as illustrated in FIG. 9, a single computer (a first computer 903) may be used by both the first technician 901 and second technician 902 to perform the filling process. For example, the first technician 901 may perform the filling process for a prescription or for a plurality of prescriptions at the first computer and when the filling process is finished, a second technician may use the first computer 903 to perform inspection and verification. Authentication for both the first and second technician may be performed on the single computer 903.

Figure 10:
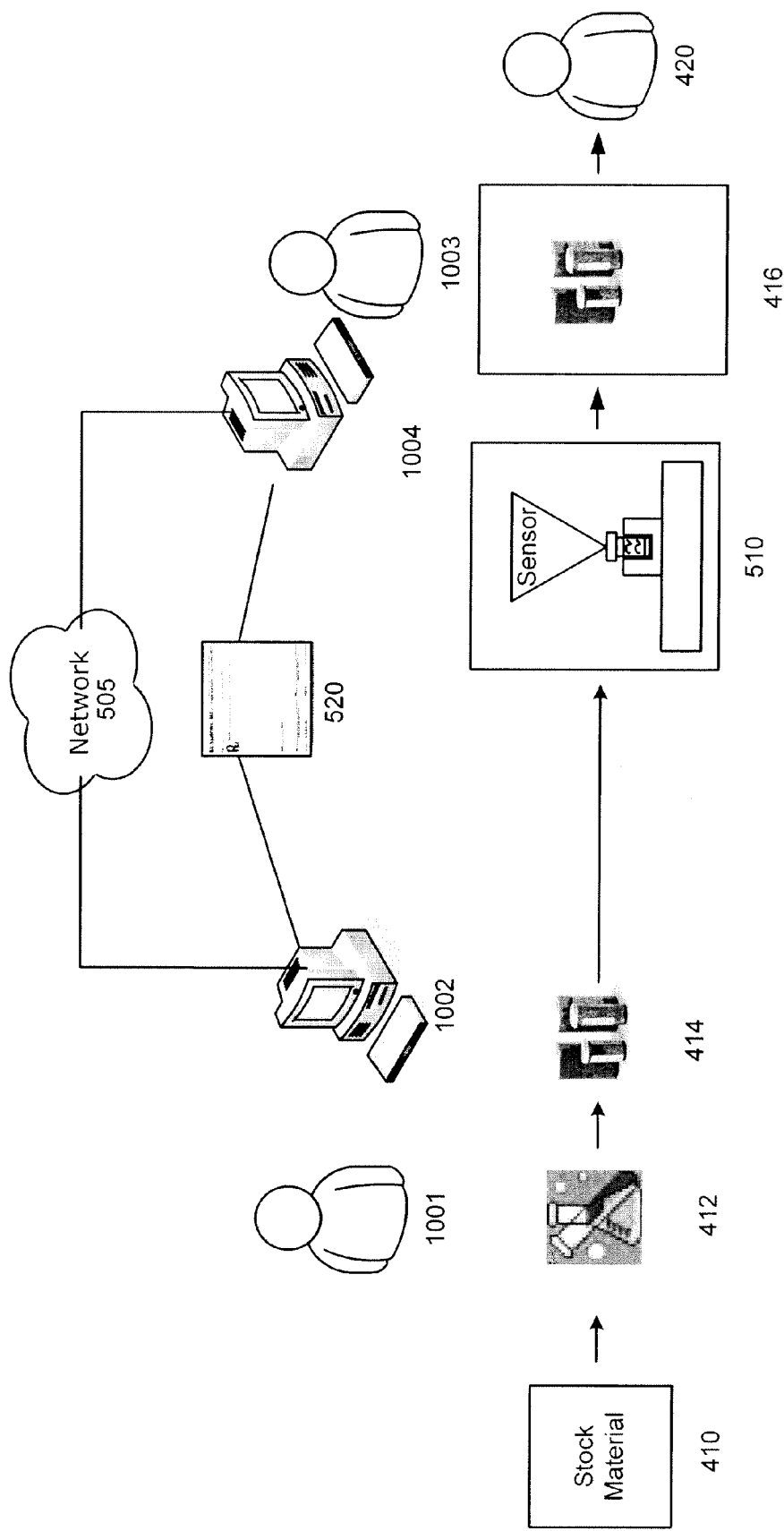
FIG. 10 illustrates an embodiment of the system using two computers and two technicians.

Alternatively two computers may be used, as illustrated in FIG. 10. For example, a first technician 1001 may perform the filling process for a prescription of for a plurality of prescriptions at a first computer 1002 while a second technician 1003 may use a second computer 1004 to perform inspection and verification. The first computer 1002 and second computer 1003 may be located in different areas of the pharmacy resource. Authentication of the first technician 1001 may be performed at the first computer 1002 and authentication of the second technician 1003 may be performed at the second computer 1004.

Figure 11:
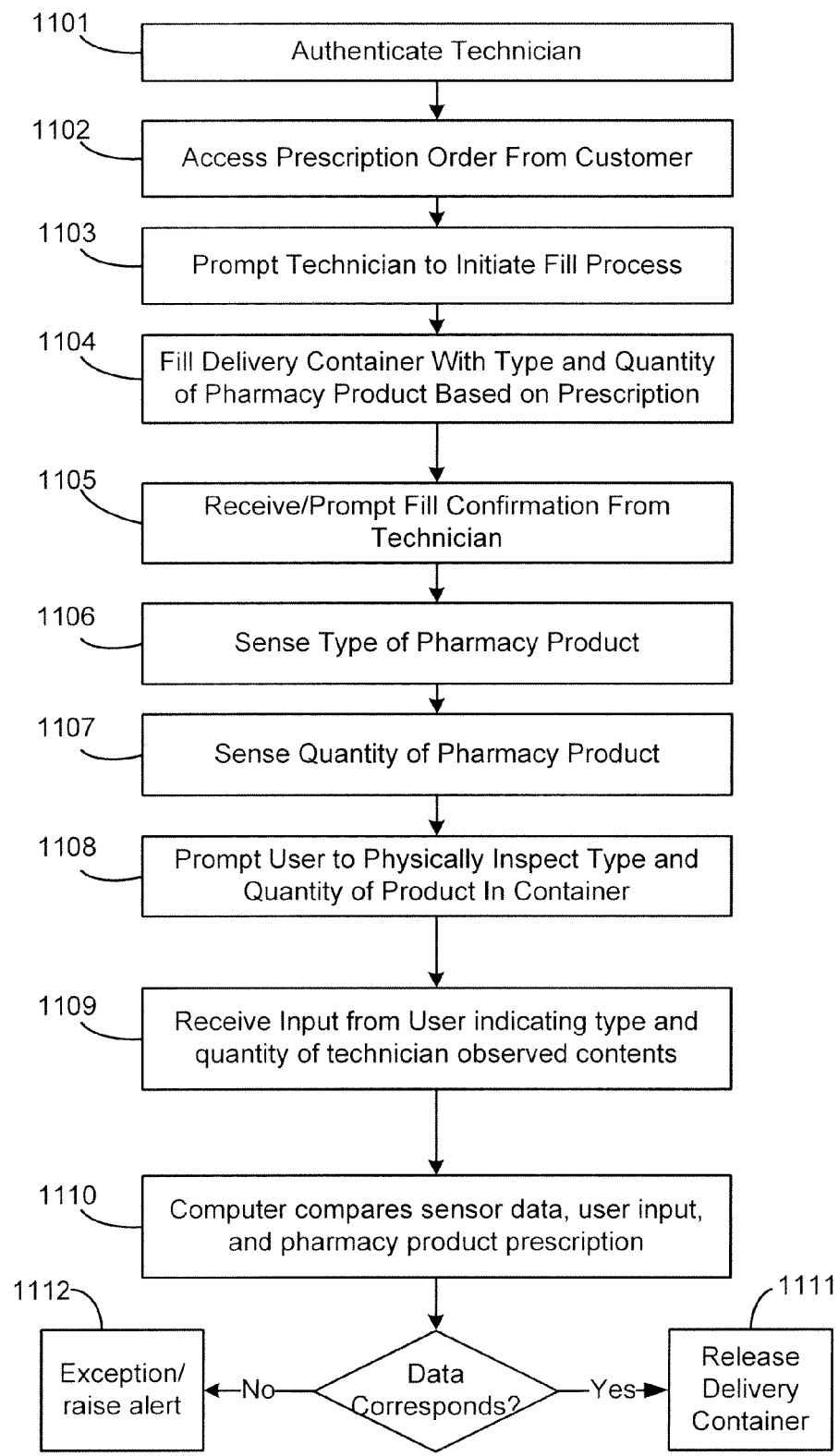
FIG. 11 illustrates a second process embodiment.

FIG. 11 illustrates a specific embodiment of the method described above for general pharmacy filling. At a first block 1101 a single technician is authenticated to the pharmacy computing system. Access to a first prescription 1102 is provided to the computing system. At the next block 1103, the authenticated technician may be prompted to begin filling a prescription order. Prompting the technician may include indicating (e.g., by displaying on a computer monitor) to the technician a pharmacy prescription order (e.g., type of product and quantity) to be filled. Prompting the technician may involve identifying pharmacy prescription order information. Prompting may also involve printing out a label that indicates how the pharmacy product order is to be tilled (e.g., type of product and quantity). Prompting the technician may also involve merely indicating a successful authentication session for a particular, pharmacy prescription order, where the technician may have been informed of the prescription data at a time prior to authentication or by another means (e.g., physical paper showing a listing of prescriptions and corresponding filling information). At block 1104, the technician fills a delivery container with a type and quantity of pharmacy product based on the accessed pharmacy product prescription. At block 1105, the computing system may prompt for confirmation that the delivery product has been placed in the delivery container and/or prompt an authenticated technician to scan the container. Alternatively, the computer may be programmed to detect whether the delivery container has been placed in a receptacle (configured for the delivery container) and proceed to blocks 1106 and 1107. At block 1106 and 1107 the computing system may use electronic sensors coupled to the pharmacy computing system to take sensor measurements of the contents of the delivery container. A first sensor may be used to detect the type of pharmacy product 1106. The first sensor may be a spectrographic emitter and sensor combination that determines the chemical composition of the contents by refracting/reflecting specific light off the content. The first sensor may be an image sensor that captures an image of the product. In this case, the pharmacy computing system may execute optical recognition software that is able to compare the sensed image of the product with products images in a database.

A second sensor may be used to determine the quantity of the pharmacy product in the delivery container 1107. The second sensor may be a scale or weight sensor. In this case, the weight and a known density of the product (as identified from the first sensor) may be used to determine the quantity of the product in the delivery container. Alternatively, the second sensor may be an infrared sensor that can detect the quantity of product.

After the sensing process is performed, the pharmacy computing system may prompt the technician to begin physical inspection of the delivery container 1108. The system may then prompt the technician to input the results of the technician's observations 1109. This may be performed using any of the interaction mechanisms described above. After receiving the sensor readings and the technician observed readings, the computer may compare data from the sensor readings and the technician entered observations with the actual prescription data 1110. If there are no discrepancies, then the computer may indicate a release of the delivery container to a customer 1111. If there are any discrepancies, an exception may be thrown 1112. In one embodiment, an additional process that may be performed during the filling and verification process is a drug utilization review (DUR). In the DUR process the computing system and/or a pharmacist may review the pharmacy prescription order against a database for adverse effects such as allergies, drug interactions, etc. For example, the database may contain customer allergy information and the computer may raise an alert if the pharmacy product prescription may cause an allergic reaction for a customer. Also, in pharmacy prescription orders involving two or more different drugs, the DUR process may check to make sure that the combination of drugs will not cause an adverse interaction and raise an alert.

Figure 12:
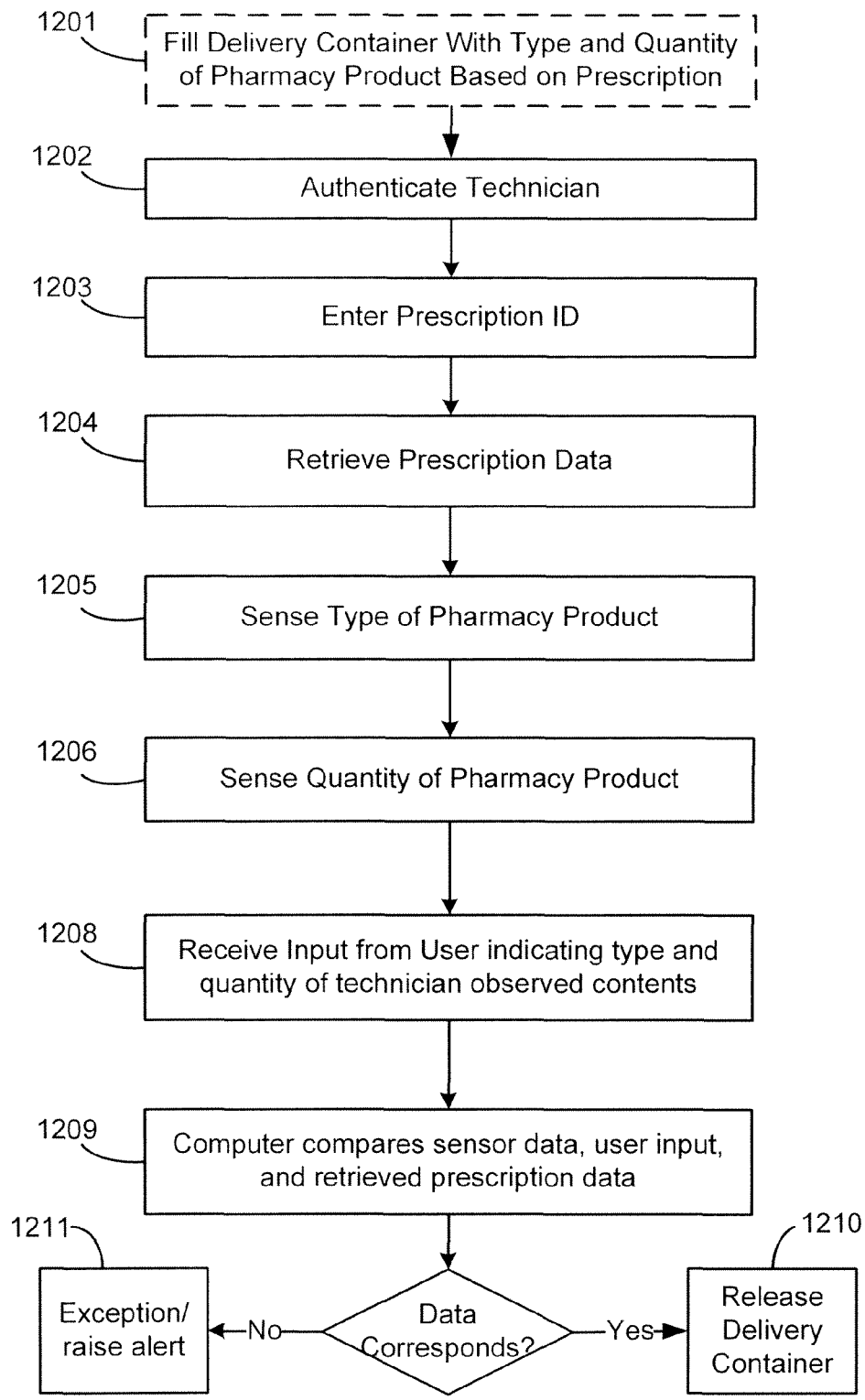
FIG. 12 illustrates a third process embodiment.

FIG. 12 illustrates another specific embodiment of the method described above for general pharmacy filling. At block 1201, shown in dashed lines, a technician may fill a delivery container with a type and quantity of pharmacy product based on a prescription. At a block 1202 a single technician may be authenticated to the pharmacy computing system. It should be noted that the physical filling 1201 of a prescription may occur before authentication or after authentication, but may occur, in this embodiment, without a prompt from the first computer. For example, the technician may be given a physical document listing a set of prescriptions with their corresponding filling instructions (e.g., type of drug and quantity). At block 1203, the technician may enter a prescription identifier for a verification process. The pharmacy computing system (e.g., at a first computer) may retrieve prescription data based on the prescription identifier 1204.

At blocks 1205 and 1206 the computing system may use electronic sensors coupled to the pharmacy computing system to take sensor measurements of the contents of the delivery container. A first sensor may be used to detect the type of pharmacy product 1205. A second sensor may be used to determine the quantity of the pharmacy product in the delivery container 1107. The first and second sensors may include any of the sensors described above. The pharmacy computing system may be programmed to receive input from a user indicating the type and quantity of the pharmacy product contained in the delivery container 1208 based on a physical inspection by the technician. It should be noted that any of the above described mechanisms for reducing psychological bias in the inspection may be implemented as well. After receiving the sensor readings and the technician observed readings, the computer may compare data from the sensor readings and the technician entered observations with the retrieved prescription data 1209. If there are no discrepancies, then the computer may indicate a release of the delivery container to a customer 1210. If there are any discrepancies, an exception may be thrown 1211.

Although the processes illustrated in the figures and described above may indicate a particular sequence, unless otherwise described, the process blocks described above may be sequenced in various orders while remaining within the scope of the described method and system.

What is claimed is:

1. A method of filling a pharmacy product prescription using a pharmacy computing system comprising:
   authenticating a non-registered pharmacist to the pharmacy computing system at a first computer to initiate a first authenticated computing session;
   automatically prompting the non-registered pharmacist by the first computer during the first authenticated computing session to fill a customer delivery container with a type and an amount of a pharmacy product based on data of a pharmacy product prescription;
   sensing with a first sensor one of the amount or type of pharmacy product contained in the delivery container using at least a first sensor after the delivery container is filled by the non-registered pharmacist;
   automatically prompting the non-registered pharmacist by one of the first computer or a second computer of the pharmacy computing system to inspect one of the amount or type of pharmacy product contained in the delivery container after a first predetermined period has elapsed and after the sensing is performed using the first sensor, wherein the automatic prompting by the one of the first computer or the second computer includes generating a display that initiates an interaction mechanism between the non-registered pharmacist and the one of the first computer or the second computer to remove an influence of prior memory bias of the previous fill of the customer delivery container on the non-registered pharmacist;
   receiving an input into the pharmacy computing system entered by the non-registered pharmacist viewing the generated display during the first authenticated computing session after the first predetermined period has elapsed and after the sensing is performed using the first sensor, wherein the input indicates one of the amount or type of pharmacy product contained in the delivery container based on inspection of the delivery container by the non-registered pharmacist;

indicating a release status for the delivery container based on the first sensor data, the entered input from the non-registered pharmacist, and the data of the pharmacy product prescription.

2. The method of claim 1, wherein the first predetermined period of time includes a duration of the sensing using the first sensor of the pharmacy product in the delivery container.

3. The method of claim 1, wherein the first predetermined period is set based on a duration of the sensing of the pharmacy product in the delivery container.

4. The method of claim 1, wherein prompting the non-registered pharmacist to fill a customer delivery container comprises printing out a pharmacy product prescription label.

5. The method of claim 1, further comprising alerting a registered pharmacist of a discrepancy between any of the first sensor data, the entered input, or the pharmacy product prescription data.

6. The method of claim 1, wherein authenticating a non-registered pharmacist to the pharmacy computing system comprises periodically prompting the non-registered pharmacist to enter credentials to maintain validity of the authenticated computing session.

7. The method of claim 1, wherein authenticating a non-registered pharmacist to the pharmacy computing system comprises using at least one biometric sensor to identify the non-registered pharmacist.

8. The method of claim 1, wherein the first sensor data comprises at least one of weight data, spectrographic data, olfaction data, pH data, toughness data, tensile strength data, composition data, temperature data, humidity data, or image data.

9. A method of filling a pharmacy product prescription using a pharmacy computing system comprising:

authenticating a non-registered pharmacist to the pharmacy computing system to initiate a first authenticated computing session;

automatically prompting the first non-registered pharmacist by the computing system during the first authenticated computing session to fill a customer delivery container with a type and an amount of a pharmacy product based on data of a pharmacy product prescription;

sensing with a first sensor at least one of the amount or type of pharmacy product contained in the delivery container to provide first sensor data to the pharmacy computing system;

authenticating the non-registered pharmacist to the pharmacy computing system to initiate a second authenticated computing session after the sensing is performed using the first sensor;

automatically prompting the first non-registered pharmacist by the pharmacy computing system to inspect one of the amount or type of pharmacy product contained in the delivery container during the second authenticated computing session after a first predetermined period has elapsed, wherein the automatic prompting by the pharmacy computing system includes generating a display that initiates an interaction mechanism between the non-registered pharmacist and the pharmacy computing system to remove an influence of prior memory bias of the previous fill of the customer delivery container on the non-registered pharmacist;

receiving an input into the pharmacy computing system entered by the non-registered pharmacist viewing the generated display during the second authenticated computing session after the first predetermined period has elapsed and after the sensing is performed using the first sensor, wherein the input indicates one of the amount or type of pharmacy product contained in the delivery container based on inspection of the delivery container by the non-registered pharmacist;

indicating a release status for the delivery container based on the whether the first sensor data and the input entered by the non-registered pharmacist coincide with the pharmacy product prescription data.

10. The method of claim 9, wherein the first predetermined period of time includes a duration of the sensing using the first sensor of the pharmacy product in the delivery container.

11. The method of claim 9, wherein the first predetermined period is set based on a duration of the sensing of the pharmacy product in the delivery container.

12. The method of claim 9, further comprising alerting a registered pharmacist of a discrepancy between any of the first sensor data, the entered input, or the pharmacy product prescription data.

13. The method of claim 9, wherein the first authentication session is performed at a first area using a first computer coupled to the pharmacy computing system and the second authentication session is performed at a second area using a second computer coupled to the pharmacy computing system.

14. The method of claim 9, wherein the first authenticated computing session and second authenticated computing session are initiated on a single computer of the pharmacy computing system.

15. A method of filling a pharmacy product prescription with a pharmacy computing system comprising:

authenticating a first non-registered pharmacist to the pharmacy computing system to initiate a first authenticated computing session;

automatically prompting the first non-registered pharmacist by the computing system during the first authenticated computing session to fill a customer delivery container with a type and an amount of a pharmacy product based on data of a pharmacy product prescription;

sensing using a first sensor at least one of the amount or type of pharmacy product contained in the delivery container to provide first sensor data to the pharmacy computing system;

authenticating a second non-registered pharmacist to the pharmacy computing system to initiate a second authenticated computing session;

automatically prompting the second non-registered pharmacist by the pharmacy computing system to inspect one of the amount or type of pharmacy product contained in the delivery container after the sensing using the first sensor is performed, wherein the automatic prompting by the pharmacy computing system includes generating a display that initiates an interaction mechanism between the non-registered pharmacist and the pharmacy computing system to remove an influence of prior memory bias of the previous fill of the customer delivery container on the non-registered pharmacist;

receiving an input entered into the pharmacy computing system during the second authenticated computing session from the non-registered pharmacist indicating one of the amount or type of pharmacy product contained in the delivery container based on the inspection of the delivery container by the non-registered pharmacist; and indicating a release status for the delivery container based on whether the first sensor data and the input entered by the second non-registered pharmacist correspond to the pharmacy product prescription data.

16. The method of claim 15, further comprising sensing, after initiating the second authentication session, the at least one of the amount or type of pharmacy product contained in the delivery container to provide second sensor data to the pharmacy computing system and wherein indicating a release status is based on whether the type and amount of the pharmacy product indicated by the first sensor data, the second sensor data, and the input entered by the second non-registered pharmacist correspond to the pharmacy product prescription data.

17. The method of claim 15, wherein the first authentication session is performed at a first area using a first computer coupled to the pharmacy computing system and the second authentication session is performed at a second area using a second computer coupled to the pharmacy computing system.

18. The method of claim 15, wherein the first authenticated computing session and second authenticated computing session are initiated on a single computer of the pharmacy computing system.

19. A system for enabling pharmacy product filling and dispensing to be performed by a single non-registered pharmacist comprising:
 a first computer adapted to store data on a pharmacy product prescription;
 a receptacle for receiving a delivery container corresponding to the pharmacy product prescription;
 a first sensor coupled to the first computer and adapted to create image data of a pharmacy product contained in the delivery container; and
 a second sensor coupled to the first computer and adapted to provide weight data of the pharmacy product contained in the delivery container;
 wherein the first computer is adapted to store and execute a set of program instructions, wherein the program instructions, when executer, cause the computer to:
 authenticate a non-registered pharmacist to the pharmacy computing system at a first computer to initiate a first authenticated computing session,
 prompt the non-registered pharmacist during the authenticated computing session to fill a customer delivery container with a type and an amount of a pharmacy product based on the pharmacy product prescription data;
 calculate an amount and type of pharmacy product contained in the delivery container using the first and second sensor after the delivery container is filled by the non-registered pharmacist,
 prompt the non-registered pharmacist to inspect one of the amount or type of pharmacy product contained in the delivery container after a first predetermined period has elapsed and after the calculation is performed using the first sensor and second sensor, wherein the prompt includes generation of a display that initiates an interaction mechanism between the non-registered pharmacist and the first computer to remove an influence of prior memory bias of the previous fill of the customer delivery container on the non-registered pharmacist,
 receive an input entered into the pharmacy computing system during the first authentication session by the non-registered pharmacist indicating the amount and type of pharmacy product contained in the delivery container based on inspection of the delivery container by the non-registered pharmacist, and
 indicate a release status for the delivery container based on the calculation using the first and second sensor, the entered input from the non-registered pharmacist, and the data of the pharmacy product prescription.

20. A system for enabling pharmacy product filling and dispensing to be performed by at least one non-registered pharmacist without the assistance of a registered pharmacist comprising:
 a set of computers connected to a network;
 a first sensor adapted to create image data of a pharmacy product; and
 a second sensor adapted to provide weight data of the pharmacy product;
 wherein the set of computers is adapted to execute a set of instructions that:
 authenticate a first non-registered pharmacist to initiate a first authenticated computing session,
 prompt the first non-registered pharmacist during the first authenticated computing session to fill a customer delivery container with a type and an amount of a pharmacy product based on data of a pharmacy product prescription;
 calculate an amount and type of pharmacy product contained in the delivery container using the first sensor and second sensor,
 authenticate a second non-registered pharmacist to initiate a second authenticated computing session;
 prompt the second non-registered pharmacist to inspect at least one of the amount or type of pharmacy product contained in the delivery container after the sensing is performed; wherein the prompt includes generation of a display that initiates an interaction mechanism between the second non-registered pharmacist and the set of computers to remove an influence of prior memory bias of the previous fill of the customer delivery container on the second non-registered pharmacist;
 receive an input from the second non-registered pharmacist viewing the generated display during the second authenticated computing session indicating at least one of the amount or type of pharmacy product contained in the delivery container based on the inspection of the delivery container by the second non-registered pharmacist;
 indicate a release status for the delivery container based on the whether the first sensor data, second sensor data, and the input entered by the second non-registered pharmacist correspond to the pharmacy product prescription data.

21. A method of filling a pharmacy product prescription using a pharmacy computing system comprising:
 authenticating a non-registered pharmacist to the pharmacy computing system by a computer to initiate a first authenticated computing session;
 receiving an input into the computer entered by the non-registered pharmacist of an identification of a pharmacy product prescription filled by the non-registered pharmacist;
 retrieving, by the computer, data of the pharmacy product prescription based on the identification;
 sensing with a sensor one of the amount or type of pharmacy product contained in a delivery container after the delivery container is filled by the non-registered pharmacist;
 receiving an input entered by the non-registered pharmacist viewing a computer generated display into the computer during the first authenticated computing session, after a predetermined period has elapsed from the receipt of the input and after the sensing is performed using the sensor, wherein the input indicates one of the amount or type of pharmacy product contained in the delivery container based on inspection of the delivery container by the non-registered pharmacist; wherein the computer generated display includes an interaction mechanism between the non-registered pharmacist and the computer to remove an influence of prior memory bias of the previous fill of the delivery container on the non-registered pharmacist;

indicating a release status for the delivery container based on data corresponding to the amount or type of pharmacy product contained in the delivery container sensed by the sensor, the entered input from the non-registered pharmacist, and the data of the pharmacy product prescription.

\* \* \* \* \*